United States Patent
Ternes et al.

(10) Patent No.: US 8,024,034 B2
(45) Date of Patent: Sep. 20, 2011

(54) PROGRAMMABLE NEURAL THERAPIES

(75) Inventors: David Ternes, Roseville, MN (US); Paul A. Haefner, Circle Pines, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 898 days.

(21) Appl. No.: 11/555,489

(22) Filed: Nov. 1, 2006

(65) Prior Publication Data

US 2008/0058901 A1    Mar. 6, 2008

(51) Int. Cl.
*A61N 1/00*    (2006.01)

(52) U.S. Cl. ............................................. 607/2; 607/59

(58) Field of Classification Search .................... 607/45, 607/2, 59
See application file for complete search history.

(56) References Cited

U.S. PATENT DOCUMENTS

| 5,179,950 | A | 1/1993 | Stanislaw |
| 6,690,974 | B2 | 2/2004 | Archer et al. |
| 2002/0077670 | A1* | 6/2002 | Archer et al. ................... 607/45 |
| 2006/0015153 | A1* | 1/2006 | Gliner et al. .................... 607/45 |
| 2006/0095081 | A1* | 5/2006 | Zhou et al. ........................ 607/2 |

* cited by examiner

*Primary Examiner* — Scott M Getzow
(74) *Attorney, Agent, or Firm* — Schwegman, Lundberg & Woessner, P.A.

(57) ABSTRACT

An implantable medical device (IMD) comprising a controller adapted to execute instructions included in firmware, a programmable neural therapy source adapted to provide programmable electrical neural stimulation therapy to at least one neural stimulation electrode, and a state machine included in hardware circuitry coupled to the programmable neural therapy source. When neural therapy is initiated by a firmware instruction, the state machine is configured to automatically apply power to the neural therapy source when neural therapy is initiated by a firmware instruction and automatically remove power from the neural therapy source when neural therapy is terminated by a firmware instruction.

27 Claims, 9 Drawing Sheets

PROGRAMMABLE NEURAL THERAPIES

FIELD OF THE INVENTION

This invention relates generally to the field of implantable medical devices. More particularly, the invention relates to the hardware and software used to control the operation of such devices.

BACKGROUND

Implantable medical devices (IMDs) are devices designed to be implanted into a patient. Some examples of these devices include devices with neural stimulation (NS) capability. Other examples include cardiac function management (CFM) devices such as implantable pacemakers, implantable cardioverter defibrillators (ICDs), cardiac resynchronization devices, and devices that include a combination of such capabilities. Further examples of implantable medical devices include implantable diagnostic devices, or implantable drug delivery systems.

Neural stimulation can be useful to treat neurological impairment of physiological systems of a patient such as the bladder, the upper airway, and the heart. Vagus nerve stimulation has been proposed to treat breathing disorders, gastrointestinal motility, eating disorders, obesity, anorexia, gastrointestinal tract disorders, hypertension, coma, and epilepsy.

Most implantable devices are processor controlled. Typically, the processor executes instructions contained in firmware to flexibly implement functions required by the device. Implementing functions of an IMD in firmware can have some disadvantages. As the number of functions performable by an implantable device increases, the processor may have to be constantly executing instructions to respond to external events and device initiated events. This can result in a large amount of battery power being consumed by the device. Also, events may result in electrical stimulation circuits drawing a large amount of battery power.

SUMMARY

This document discusses, among other things, systems, devices, and methods for implementing neural stimulation therapy. A device example includes a controller adapted to execute instructions included in firmware, a programmable neural therapy source adapted to provide programmable electrical neural stimulation therapy to at least one neural stimulation electrode, and a state machine included in hardware circuitry coupled to the programmable neural therapy source. When neural therapy is initiated by a firmware instruction, the state machine is configured to automatically apply power to the neural therapy source when neural therapy is initiated by a firmware instruction and automatically remove power from the neural therapy source when neural therapy is terminated by a firmware instruction.

A method example includes the acts of initiating neural stimulation therapy using at least one instruction included in firmware of an implantable medical device (IMD), automatically delivering, in response to the firmware instruction, an electrical neural stimulation therapy to a non-cardiac neural stimulation electrode using a state machine included in hardware in the IMD, and automatically applying power to a neural stimulation therapy source of the IMD using the state machine and removing power from the neural therapy source when neural therapy is terminated by the firmware.

This summary is intended to provide an overview of the subject matter of the present patent application. It is not intended to provide an exclusive or exhaustive explanation of the invention. The detailed description is included to provide further information about the subject matter of the present patent application.

DETAILED DESCRIPTION

Figure 1:
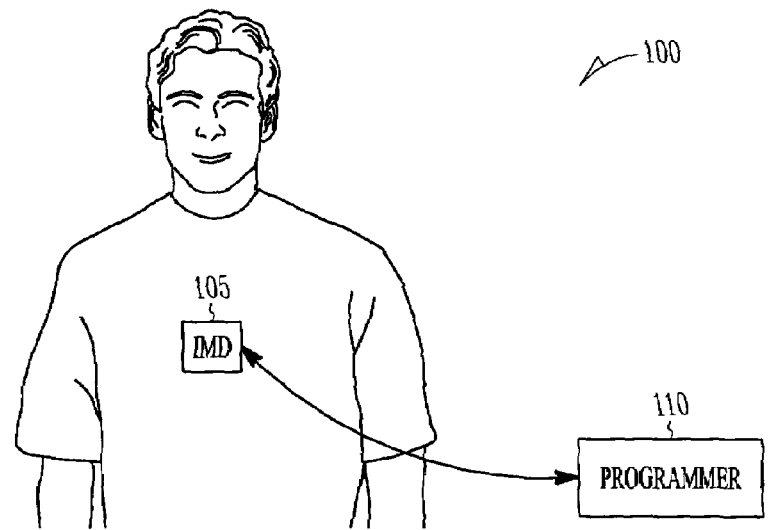
FIG. 1 illustrates portions of a system that includes an implantable medical device (IMD).

In the following detailed description, reference is made to the accompanying drawings which form a part hereof, and specific embodiments in which the invention may be practiced are shown by way of illustration. It is to be understood that other embodiments may be used and structural or logical changes may be made without departing from the scope of the present invention.

Described herein are systems, devices, and methods for implementing neural stimulation that provide the flexibility of a firmware implanted device but also provide hardware based functions to improve power efficiency.

Neural stimulation refers to the stimulation of nerve bundles in various regions of the body using electrical energy. Implantable medical devices capable of providing neural stimulation may be useful for several therapies. For example, ventricular remodeling refers to alterations in cardiac cellular structure resulting from hypertrophy of the ventricular myocardium due to increased pressure-volume in the ventricles due to a compensatory mechanism in heart failure patients. Although ventricular dilation and hypertrophy may at first be compensatory and increase cardiac output, the processes ultimately result in both systolic and diastolic dysfunction. It has been shown that the extent of ventricular remodeling is positively correlated with increased mortality in CHF patients.

Examples of methods and devices for delivering multi-site ventricular pacing therapy in conjunction with stimulation of parasympathetic nerves innervating the heart are described in Pastore et al., U.S. Pat. Application Publication No. 20050096705, entitled "Multi-site Ventricular Pacing Therapy with Parasympathetic Stimulation," filed Nov. 3, 2003, which is incorporated herein by reference. Such parasympathetic stimulation acts to decrease the stresses experienced by the ventricular walls during systole so as to prevent or reverse the cardiac remodeling which can occur in heart failure patients. The parasympathetic stimulation may be delivered by an implantable cardiac device via a bipolar electrode incorporated into a lead adapted for transvenous insertion, such as into the superior or inferior vena cava. In order to counteract a tendency of parasympathetic stimulation to reduce cardiac output, the delivery of parasympathetic stimulation may be modulated in accordance with the patient's exertion level and/or a sensed parameter related to cardiac output.

Another example of a neural stimulation therapy relates to hypertension. Hypertension is a cause of heart disease and other related cardiac co-morbidities. Hypertension occurs when blood vessels constrict. As a result, the heart works harder to maintain flow at a higher blood pressure, which can contribute to heart failure. A pressoreceptive region or field is capable of sensing changes in pressure, such as changes in blood pressure. Pressoreceptor regions can be referred to as baroreceptors, which generally include any sensors of pressure changes. For example, baroreceptors include afferent nerves and further include sensory nerve endings that are sensitive to the stretching of the wall that results from increased blood pressure from within, and function as the receptor of a central reflex mechanism that tends to reduce the pressure. Baroreflex functions as a negative feedback system, and relates to a reflex mechanism triggered by stimulation of a baroreceptor. Increased pressure stretches blood vessels, which in turn activates baroreceptors in the vessel walls.

Activation of baroreceptors naturally occurs through internal pressure and stretching of the arterial wall, causing baroreflex inhibition of sympathetic nerve activity (SNA) and a reduction in systemic arterial pressure. An increase in baroreceptor activity induces a reduction of SNA, which reduces blood pressure by decreasing peripheral vascular resistance. Direct electrical stimulation of parasympathetic nerves can activate the baroreflex, inducing a reduction of sympathetic nerve activity and reducing blood pressure by decreasing vascular resistance. Examples of systems and methods to treat hypertension using neural stimulation energy are described in Heil et al., U.S. Pat. Application Publication No. 20050149128, entitled "Baroreflex Stimulation System to Reduce Hypertension," filed Dec. 24, 2003, which is incorporated herein by reference.

FIG. 1 illustrates portions of a system 100 that includes an implantable medical device (IMD) 105. As an example, the system 100 shown is used to provide neural stimulation (NS). Examples of the IMD 105 include, without limitation, a device with neural stimulator functions only, and a device that provides a combination of NS and cardiac function management (CFM). The system 100 also typically includes an IMD programmer or other external device 110 that communicates wireless signals with the IMD 105. The external device 110 can be used to adjust a programmed electrical stimulation therapy provided by the IMD 105, and the IMD 105 can report device data (such as battery and lead resistance) and therapy data (such as sense and stimulation data) to the to the external device 110. According to some examples, the IMD 105 provides electrical energy to stimulate baroreceptors to provide NS therapy such as anti-hypertension (AHT) therapy. In some examples, the IMD 105 includes using an electrical lead that can be fed through the right ventricle similar to a cardiac pacemaker lead, and further fed into the pulmonary artery. The lead is used to stimulate baroreceptors in the pulmonary artery.

According to various embodiments, the IMD 105 includes sensing circuitry coupled to one or more electrical leads to sense automatic nervous system (ANS) activity. The ANS regulates "involuntary" organs, while the contraction of voluntary (skeletal) muscles is controlled by somatic motor nerves. Examples of involuntary organs include respiratory and digestive organs, and also include blood vessels and the heart. The sensed ANS activity can include, in certain examples, one or more indications of autonomic balance between sympathetic and vagal nervous systems. An ANS sensor can be used to perform feedback in a closed loop control system. For example, ANS sensors can be used to sense surrogate parameters, such as respiration and blood pressure, which are indicative of ANS activity.

In some examples, the IMD 105 provides NS therapy by generating a baroreflex electrical stimulation signal to activate the baroreflex and induce a reduction of sympathetic nerve activity. An electrical lead is adapted to be electrically connected to the IMD 105 and to be intravascularly fed into a heart. The lead includes an electrode to be positioned in or proximate to the heart to deliver the baroreflex signal to a baroreceptor region in or proximate to the heart. In some examples, the IMD includes sensing circuitry to sense one or more physiological parameters regarding an efficacy of the baroreflex therapy and provide a signal indicative of the efficacy of the baroreflex therapy.

In some examples, the IMD 105 provides electrical stimulation to the parasympathetic nerves to provide NS therapy to prevent or reverse the cardiac remodeling. In some examples, the IMD 105 further includes cardiac stimulation capabilities, such as pacing and defibrillating capabilities, in addition to the capabilities to stimulate baroreceptors and parasympathetic nerves, activate the baroreflex, and sense ANS activity.

Figure 2:
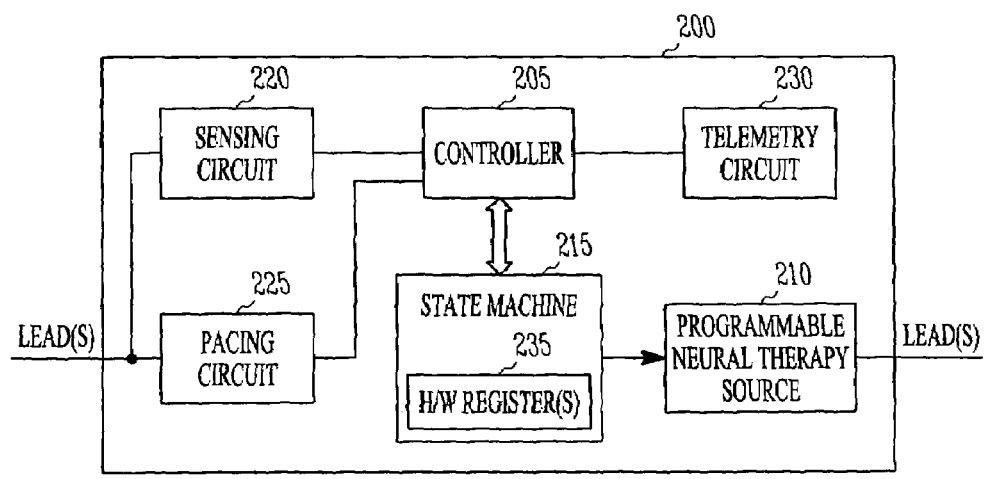
FIG. 2 is a block diagram of portions of an IMD capable of performing neural stimulation functions.

FIG. 2 is a block diagram of portions of an example of an IMD 200 capable of performing NS functions such as the IMD 105 shown in the system 100 of FIG. 1. The IMD 200 includes a controller 205, a programmable neural therapy source 210, and a state machine 215. The controller 205 executes instructions included in firmware. In some examples, the controller 205 includes a processor. The processor may be a digital signal processor, ASIC, microprocessor, or other type of processor.

The programmable neural therapy source 210 provides programmable electrical NS therapy to at least one NS electrode. In some examples, programmable neural therapy source 210 is coupled to one or more leads and the NS electrode includes a lead electrode. In some examples, the programmable neural therapy source 210 includes a programmable voltage source and the voltage is applied between two electrodes in contact with the patient. In some examples, the programmable neural therapy source 210 includes a programmable current source/sink.

Figure 3:
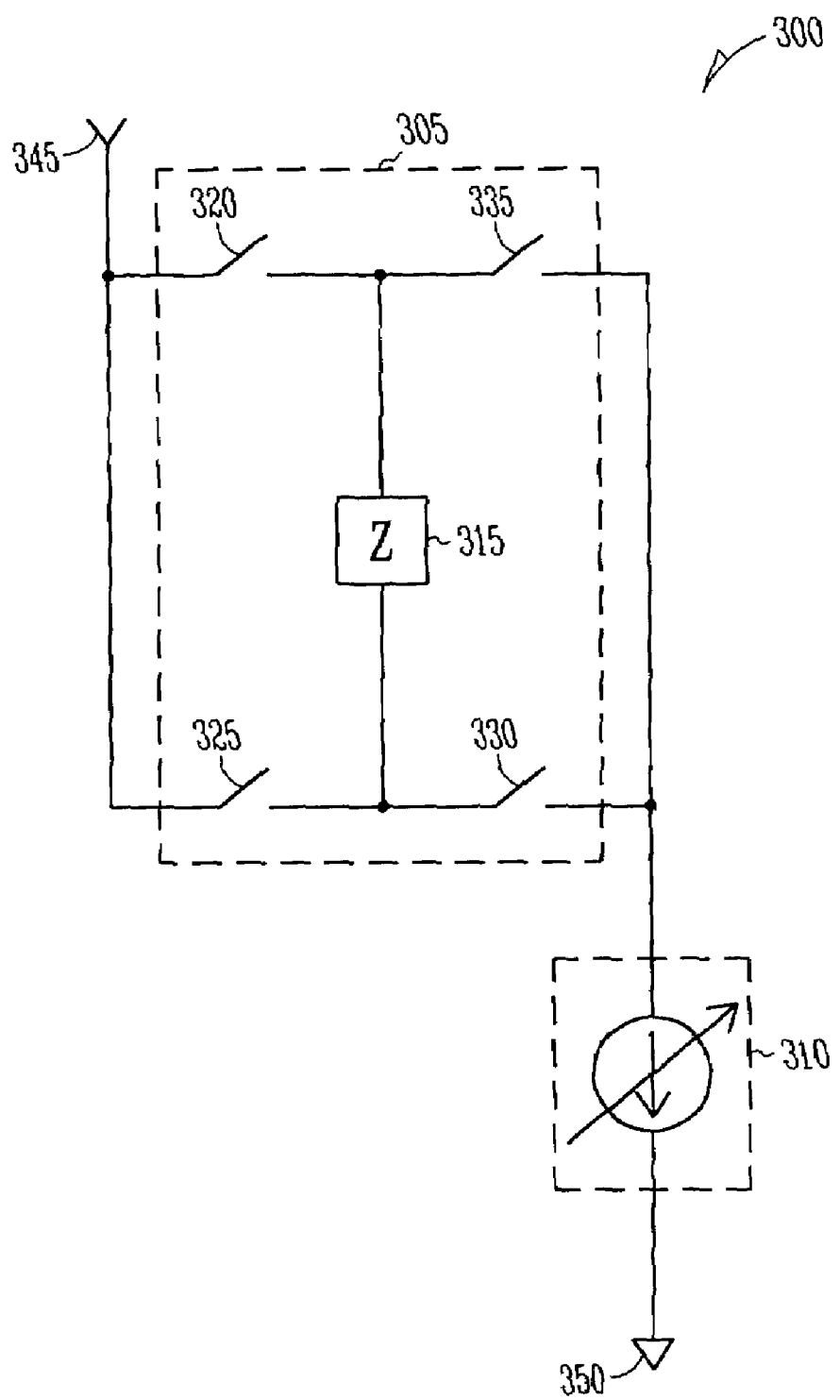
FIG. 3 shows an example of a programmable current source.

FIG. 3 shows an example of a programmable current source 300. A programmable current sink 310 causes current to flow from the input 345 through the H-bridge circuit 305 to ground 350. The H-bridge circuit 305 is in electrical communication with electrodes to be implanted into a patient, and the impedance 315 represents the impedance due to patient tissue. The impedance 315 may vary from patient to patient, and may change for one patient during the NS therapy. If switches 320, 330 are closed and switches 325, 335 are open, current flows through the patient in one direction. If switches 325, 335 are closed and switches 320, 330 are open, current flows through the patient in the other direction. The programmable current sink 310 sets the amount of current that flows in the NS. The amount of current is set by a controller. In some examples, the current is programmable by enabling one or more current mirrors. The programmed current is then mirrored in the programmable current sink 310. In some examples, the current is programmable by using a predetermined stable voltage across a set of programmable resistors.

Changing the resistance changes the current in the programmable current sink 310.

Returning to FIG. 2, various circuit components of the programmable neural therapy source 210 require a stable power source. The power source is typically provided by a power circuit and the circuit power is often referred to as $V_{DD}$. The circuit components may include switches, current mirrors, voltage references, and buffers. The state machine 215 is implemented in hardware circuitry and is coupled to the programmable neural therapy source 210. The state machine 215 automatically controls delivery of the neural therapy when delivery is initiated by one or more firmware instructions in the controller 205. When neural therapy is initiated, the state machine 215 automatically applies $V_{DD}$ power to the programmable neural therapy source 210 when neural therapy is initiated by a firmware instruction and automatically removes power from the neural therapy source when neural therapy is terminated by a firmware instruction. In some examples, the state machine 215 automatically applies $V_{DD}$ power to the programmable neural therapy source 210 during an active portion of a therapy duty cycle, and automatically removes power from the neural therapy source when exiting the active portion of a therapy duty cycle. This is shown in FIG. 4.

Figure 4:
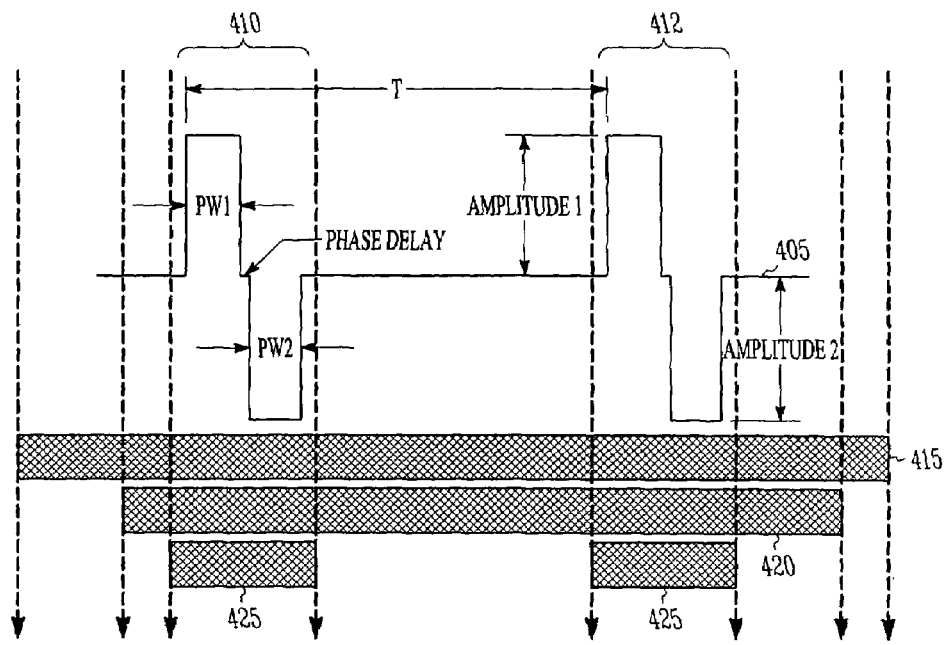
FIG. 4 shows a portion of a neural stimulation waveform showing two pulses and enable options to provide power to a programmable neural therapy source.

FIG. 4 shows a portion of a NS waveform 405 showing two pulses 410, 412. The pulses 410, 412 shown are biphasic to promote charge balance at the tissue interface, but monophasic pulses may also be used. Using biphasic pulses to promote charge balance is also useful in limiting corrosion of electrodes. The parameters of the waveform 405 are determined by the state machine 215. The positive going pulse width (PW1) is a separate parameter from the negative going pulse width (PW2), as is the positive pulse amplitude (Amplitude 1) from the negative going amplitude (Amplitude 2). Other parameters include the period (T) of the pulses 410, 412, and the inter-pulse phase delay.

FIG. 4 also shows three options for enables 415, 420, 425 that the state machine 215 may use to provide power to the programmable neural therapy source 210. In some examples, power is applied to the programmable neural therapy source 210 when the firmware instructs the state machine 215 to begin therapy and ends when the firmware instructs the state machine 215 to end therapy. This may be represented by the first enable 415. Power may also be applied to the programmable neural therapy source 210 during an active portion of a neural therapy duty cycle and removed during an inactive portion of a neural therapy duty cycle. Therefore, the first enable 415 may also represent the case where the active portion of the therapy duty cycle is defined by a number of associated bursts of electrical stimulation pulses. This option is further illustrated in FIG. 5A. The active portion of the therapy duty cycle is defined by the six bursts of stimulation pulses. An inactive portion of the therapy duty cycle commences when delivery of the bursts has finished. The state machine 215 applies power to the programmable neural therapy source 210 before the first burst 510 and removes power after the last burst.

In the second enable 420 in FIG. 4, power is applied only during a burst of stimulation pulses. When instructed by the firmware, the state machine 215 enables power to the programmable neural therapy source 210 while delivering a burst of electrical neural therapy stimulation pulses, and the state machine 215 removes power after the burst. This option is further illustrated in FIG. 5B. As in FIG. 5A, the therapy is defined by six bursts of electrical neural therapy stimulation pulses. In this option, the active portion of the therapy duty cycle is defined by a burst 530 of associated electrical neural therapy stimulation pulses. The state machine 215 applies power to the programmable neural therapy source 210 during each burst 530 and removes power from the neural therapy source 210 after each burst 530.

In the third enable 425 in FIG. 4, power is applied only during an electrical neural therapy stimulation pulse. When instructed by the firmware, the state machine 215 enables power to the programmable neural therapy source 210 while delivering an electrical neural therapy stimulation pulse 410, and the state machine 215 removes power after the pulse. This option is further illustrated in FIG. 5C. In this option, the active portion of the therapy duty cycle is defined by an electrical neural therapy stimulation pulse 535. The state machine 215 applies power to the programmable neural therapy source 210 during each pulse and removes power from the neural therapy source 210 after each pulse.

It takes a certain amount of time for the various circuit components of the programmable neural therapy source 210 to reach a powered-up state. Therefore, power is supplied to the programmable neural therapy source 210 during an interval that can be viewed as an envelope of time around the active portion of a therapy duty cycle. The envelope of time begins a sufficient amount of time before the active portion to activate the programmable neural therapy source 210 and place it in a powered-up state, and ends when the active portion of a therapy duty cycle ends or just afterwards. In FIG. 4, if the active portion of the duty cycle is defined by the biphasic stimulation pulse 410, it can be seen that the enable 425 begins before delivery of the pulse 410. The power can be removed as the pulse width ends or after it ends. In some examples, the state machine 215 applies power to the programmable neural therapy source 210 within a range of approximately ten microseconds (10 μs) to five milliseconds (5 ms) before the active portion of a therapy duty cycle. The state machine 215 may apply power to the programmable neural therapy source 210 approximately eighty microseconds (80 μs) before the active portion of a therapy duty cycle.

It may be desirable to have the controller 205 override the state machine 215. In some examples, one or more firmware instructions instruct the controller 205 to override the state machine 215 and maintain the programmable neural therapy source 210 in a powered-up condition until the firmware override is removed.

According to some examples, the IMD 200 is a combination medical device and is capable of performing cardiac function management (CFM) as well as performing NS functions. In some examples, the IMD 200 includes a cardiac signal sensing circuit 220 and a pacing circuit 225 coupled to one or more cardiac leads. The cardiac signal sensing circuit 220 produces a signal representative of cardiac activity of a subject and the pacing circuit 225 delivers an electrical stimulation pulse to one or more pacing electrodes. In some examples, the cardiac signal sensing circuit 220 includes a protection switch to disconnect the circuit during delivery of pacing or NS therapy. In some examples, the controller 205 provides NS therapy in response to the sensed cardiac signals. The IMD may also include a telemetry circuit 230 to communicate wirelessly with an external device.

Because the state machine 215 automatically controls delivery of the neural therapy, the firmware does not need to intervene once the therapy is set up and initiated. IMDs are battery powered. Typically, a dedicated state machine requires less power to run than a general purpose processor. Because the controller 205 can be idled after initiating the NS therapy, battery power of the IMD may be saved. Another approach is to free up the controller 205 for other tasks once the NS therapy is initiated. This results in device flexibility.

According to some examples, the state machine 215 includes one or more hardware registers 235 writeable by the controller 205. Firmware instructions are executed that write one or more one or more fields in the hardware registers 235 to define the programmable electrical neural stimulation therapy. Examples of parameters that can be set by the hardware registers include, among other things, pulse width times, delay between pulses, pulse amplitudes, the number of pulses delivered in the therapy, and the number of pulses to be included in a burst. The hardware registers 235 can be written by the firmware before NS therapy is initiated or while NS therapy is being delivered. Thus, the firmware can be written to vary a NS therapy at various times throughout the day, or to provide different therapies on different days.

Figure 6:
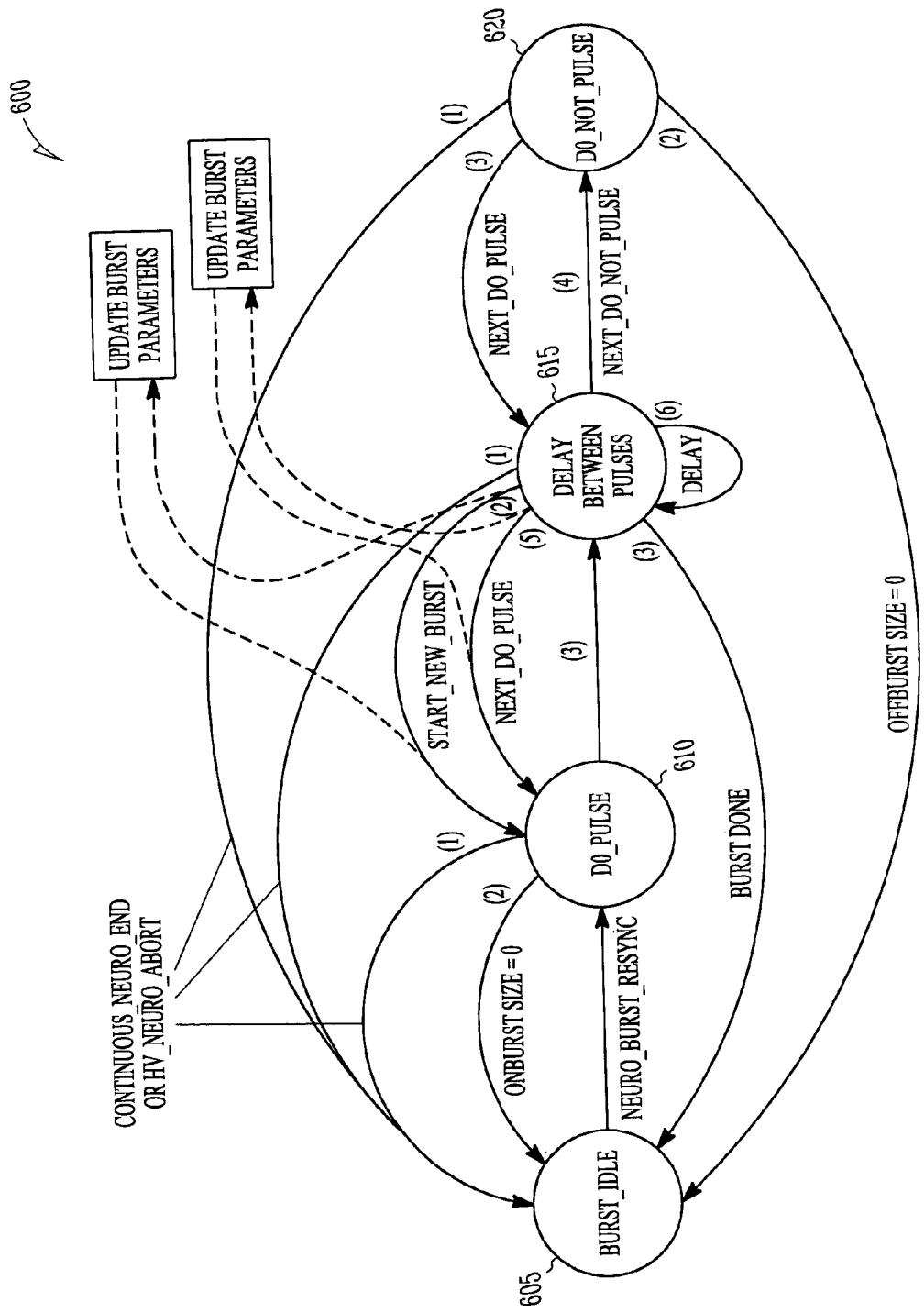
FIG. 6 shows an example of a state diagram for a state machine.
Figure 7:
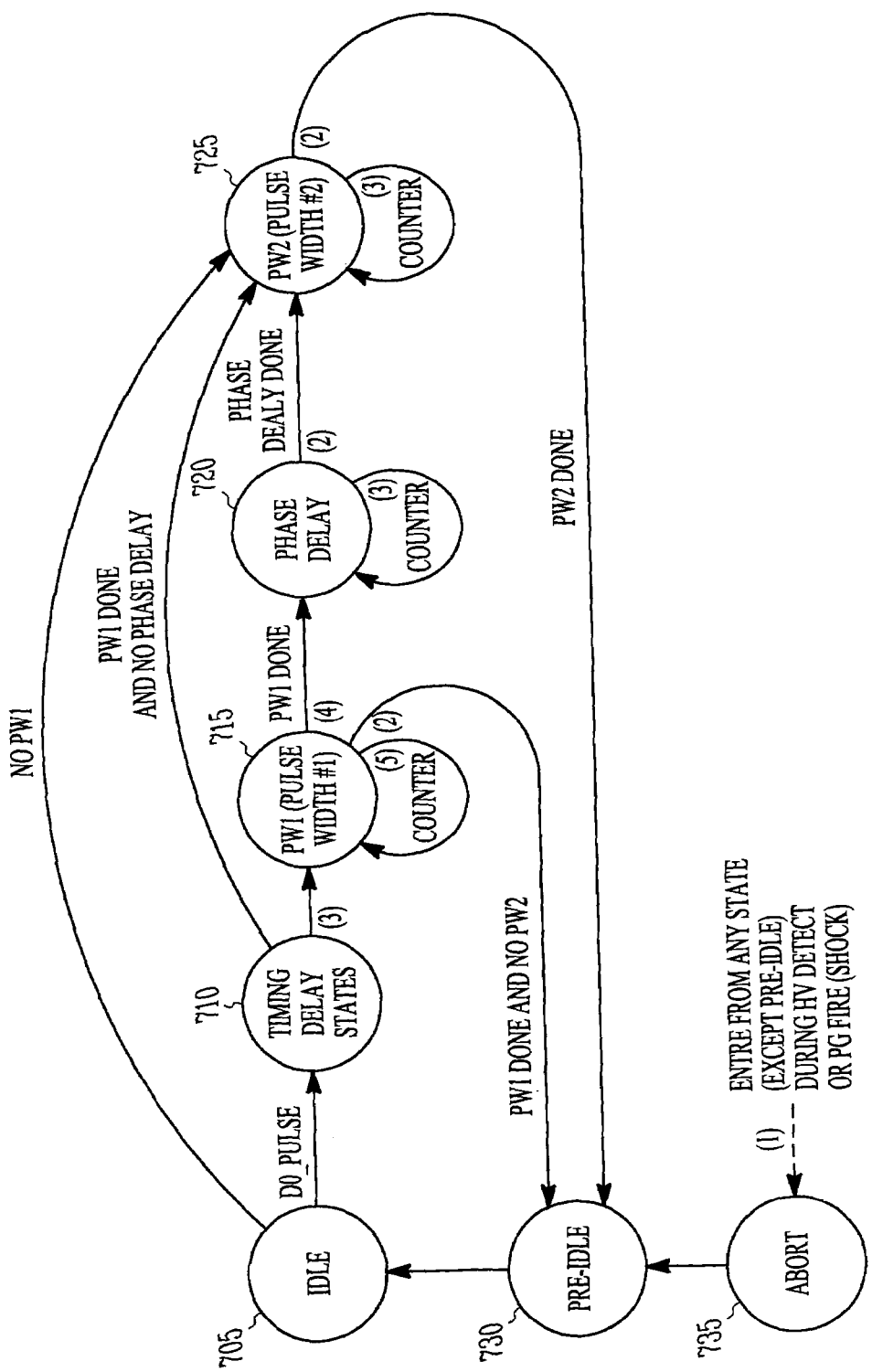
FIG. 7 shows another example of a state diagram for a state machine.

An example of a state diagram 600 for a hardware state machine is illustrated in FIG. 6. At state 605 a burst of NS therapy is not being applied and the state machine is idle either because therapy was not initiated by the firmware or because a burst is not being applied. At pulse state 610, the state machine applies a pulse of electrical stimulation energy. An example of a state diagram implementing pulse state 610 is shown in FIG. 7. An example of a biphasic stimulation pulse 410 is shown in FIG. 4. At 710, the state machine leaves idle state 705 and enters a time delay state. In some examples, a power enable is activated and this delay is sufficient to allow the programmable neural therapy source to be powered up. At 715, PW1 is timed. At 720, an inter-phase delay is timed. This inter-phase delay may be zero. At 725, PW2 is timed. In some examples, the firmware writes a field in a hardware register to set a pulse width and the inter-phase delay. A timer is used to time the durations. The state machine may enter pre-idle state 730 after timing either PW1 or PW2. In some examples, an abort state 735 is entered when high voltage (HV) is detected by high voltage sense circuitry or when high energy shock therapy is being initiated by the IMD.

Returning to FIG. 6, a time delay duration between delivery of pulses is timed in state 615. The state machine alternates between states 610 and 615 during the active portion of a therapy duty cycle. The state machine alternates between states 620 and 615 during an inactive portion of a therapy duty cycle. In this way, the inactive time can be measured by a number pulse times. In some examples, the number of pulses to be included in the active portion of a therapy duty cycle and the number of pulse times to be included in an inactive portion of a therapy duty cycle can be entered into fields of one or more hardware registers by the firmware. When a burst is finished, the state machine returns to idle state 605. In some examples, the state machine removes power from a programmable NS therapy source.

Figure 8:
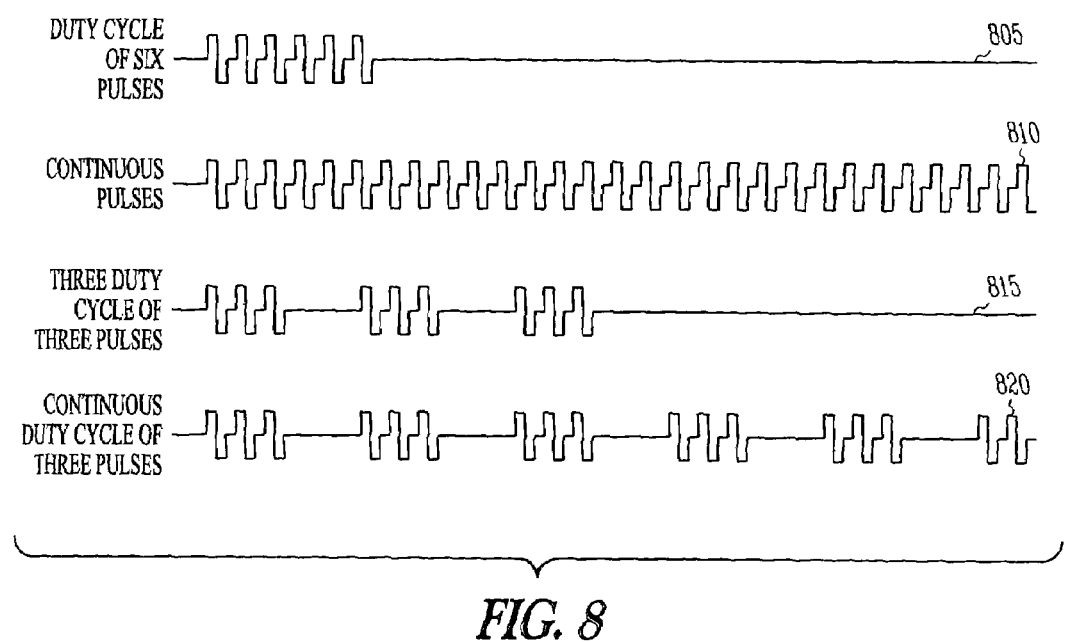
FIG. 8 shows examples of neural stimulation therapy waveforms.

The state diagram in FIG. 6 allows flexibility in defining NS therapies. FIG. 8 shows examples of NS therapy waveforms that can be delivered using the state diagram 600. The waveform delivered is determined by firmware writing one or more fields of one or more hardware registers. Waveform 805 illustrates a single burst of six electrical stimulation pulses delivered. Waveform 810 illustrates continuous delivery of pulses. Waveform 815 illustrates three duty cycles. The duty cycles include a burst of three pulses. The number of pulses in a burst, the inter-burst delay, and the number of bursts are determined by writing fields in hardware registers. In some examples, the duty cycles issue upon a NS therapy trigger from the controller. Waveform 820 illustrates continuous duty cycles issuing that include a burst of three pulses.

Figure 9:
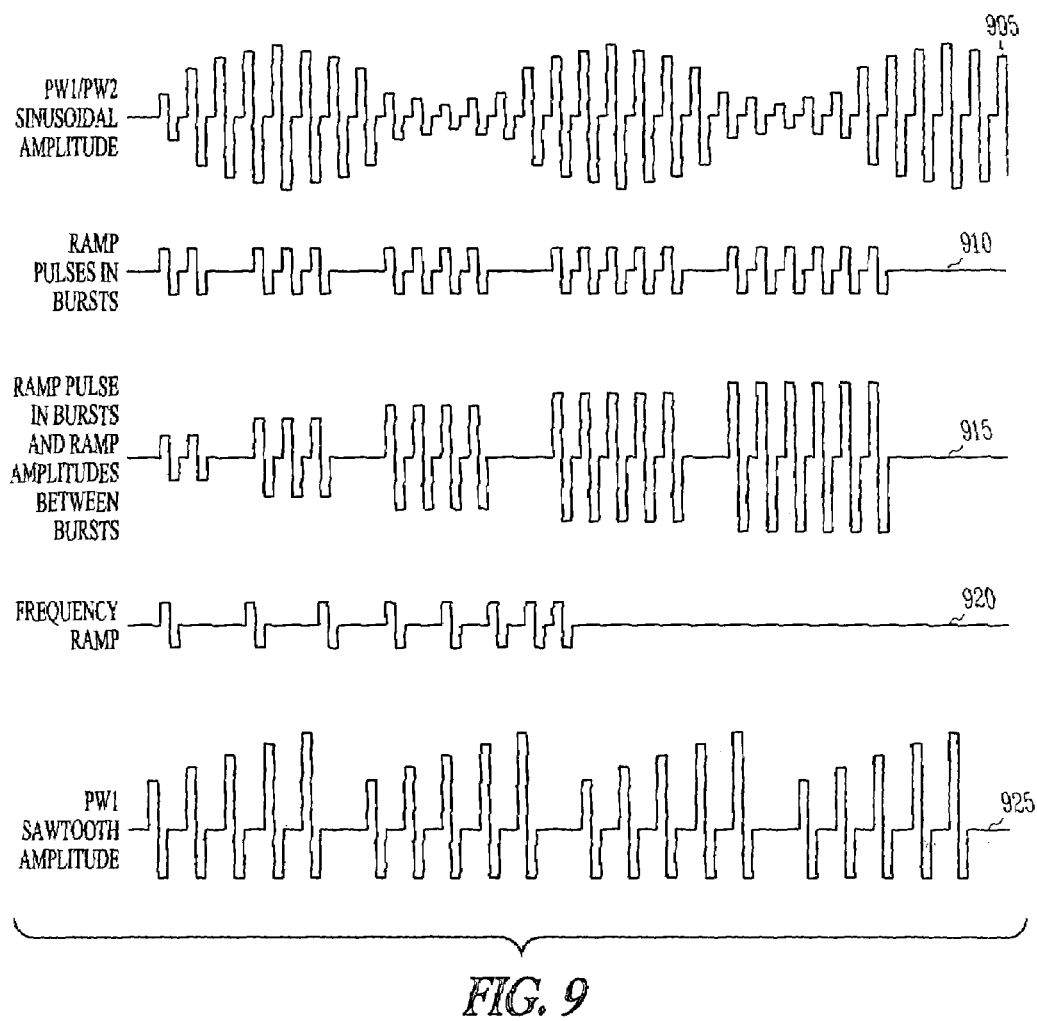
FIG. 9 shows additional examples of neural stimulation therapy waveforms.

FIG. 9 shows additional examples of NS therapy waveforms. The waveforms shown in FIGS. 8 and 9 are a non-exhaustive set of examples of possible waveforms. The amplitudes of the electrical stimulation pulses can be programmed by writing hardware registers. Waveform 915 illustrates a set of bursts where the amplitudes of the positive and negative going pulses are increased with each burst. Note that the number of pulses in the burst is changing as well. Waveforms 915 and 910 illustrate therapy deliveries where the number of pulses in a burst is ramped. In the waveform of 910, the amplitude stays constant.

In some examples, the positive and negative pulse amplitudes are independently programmable. Waveform 925 illustrates a set of bursts where the positive amplitude is ramped during the burst while the negative amplitude remains constant. The waveform 925 shows that this can result in a sawtooth function. The sawtooth can also be reversed to decrease the amplitude, or the negative amplitude may be ramped. To implement the ramp, in some examples, the hardware registers may include a field to increase the pulses by a percentage during the ramp. The increase for the negative amplitude can match the positive amplitude, be different from the positive amplitude, or as in waveform 925, the increase can be set to zero. In some examples, the hardware registers include a field to program an amplitude envelope of electrical stimulation pulses included in a duty cycle. Waveform 905 illustrates a therapy delivery where the amplitude envelope is a sinusoidal function. The amplitude envelope is formed by appropriately setting the amplitude of the programmable neural therapy source. The frequency of the sinusoidal function is determined by setting a rate of increase and decrease of the pulse amplitude.

Waveform 920 illustrates a delivery of pulses where the time period between successive pulses changes, or conversely, the frequency of the pulses. In the example, the time period decreases. The concept can be extended from the time period between pulses to the time period between bursts. If the time period between bursts is decreasing, the frequency of the bursts is increasing. The concept can be further extended to pulses within a burst. In some examples, the time period between pulses within the burst can change while the inter-burst time period remains constant. Additionally, the time period between electrical pulses within a burst can be ramped up or down within a burst. Further, the time period between pulses can be changed from burst to burst.

This illustrated flexibility is useful in designing one device but allowing the device to be programmed for multiple applications. For example, an IMD may be programmed to stimulate baroreceptors in the carotid sinus, pulmonary artery, or aortic arch using short, high-frequency bursts (such as a square wave with a frequency within a range from approximately 20-150 Hz). In another example, an IMD may be used to directly stimulate the carotid sinus nerve, aortic nerve or vagus nerve with a cuff electrode. However, a clinician may not want the IMD to deliver bursts of stimulation therapy at a constant rate. Rather the clinician may want the stimulation frequency, amplitude, and/or burst frequency to rise and fall during the day to mimic a patient's natural circadian rhythm.

Figure 10:
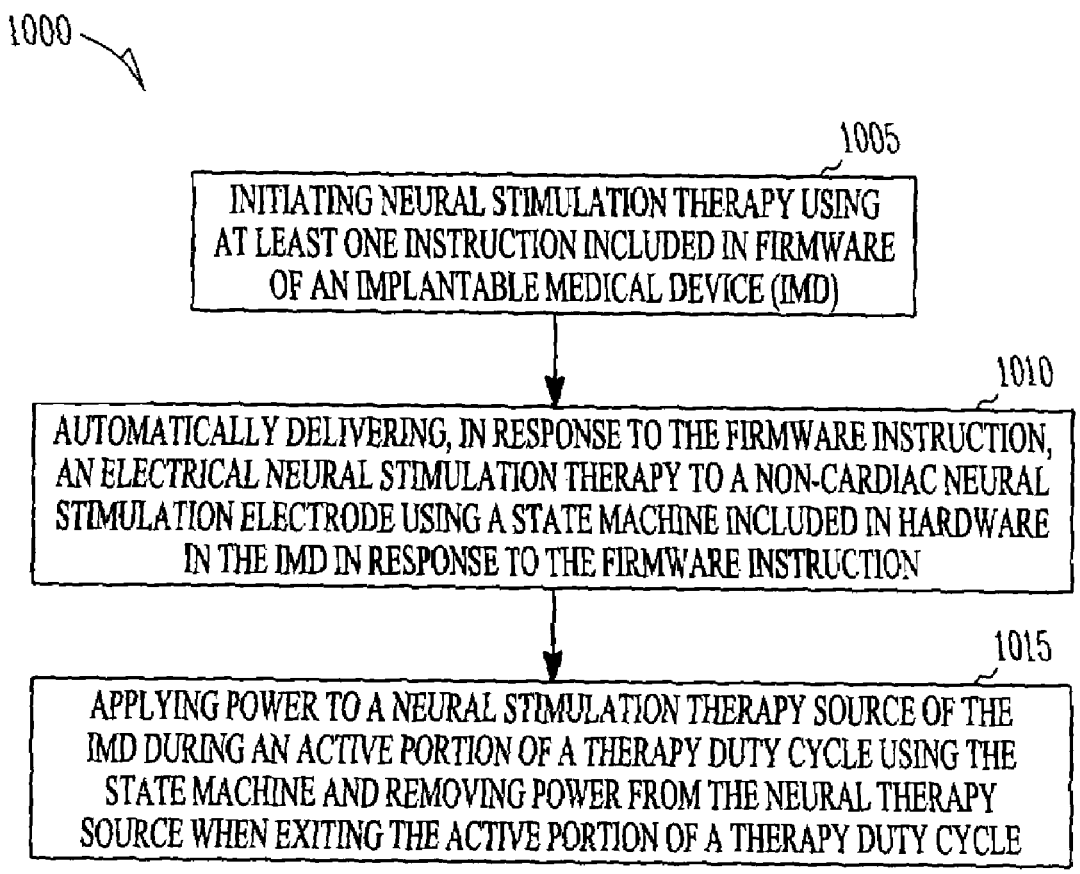
FIG. 10 illustrates a method for automatically implementing neural stimulation.

FIG. 10 illustrates a method 1000 for automatically implementing neural stimulation. At 1005, neural stimulation (NS) therapy is initiated using at least one instruction included in firmware of an implantable medical device (IMD). At 1010, in response to the firmware instruction, an electrical NS therapy is automatically delivered to a non-cardiac neural stimulation electrode using a state machine included in hardware in the IMD.

In some examples, the electrical NS therapy that is automatically delivered is programmed or defined by the firmware writing at least one hardware register in the state machine. In some examples, the method 1000 includes the firmware writing at least one hardware register to program one or more electrical stimulation pulses to be included in the active portion of a therapy duty cycle and one or more pulse times to be included in an inactive portion of a therapy duty cycle. In this way, the length of a duty cycle can be determined by timing a number of active and inactive pulses and any inter-pulse delay.

In some examples, the method 1000 includes writing at least one hardware register to program one or more duty cycles to issue upon a neural therapy trigger from a firmware instruction. Once the therapy is programmed, the firmware only has to issue the trigger to automatically commence the electrical NS therapy.

In some examples, the method 1000 includes writing at least one hardware register to programmably ramp a number of electrical stimulation pulses to be included in the active portion of a therapy duty cycle. A ramping of the number of pulses is shown in waveform 910 of FIG. 9. The number of electrical stimulation pulses in the active portion of a therapy duty cycle, or a burst, is ramped from two to six. The inactive portion of the duty cycle is the delay between bursts. In some examples, the amplitude of the pulse may also be increased with each burst. This is shown in waveform 915 of FIG. 9.

In some examples, the method 1000 includes writing at least one hardware register to program an amplitude envelope function of electrical stimulation pulses in a duty cycle. In some examples, the amplitude function is a sinusoidal function such as waveform 905 in FIG. 9. In some examples, the amplitude function is a sawtooth function such as waveform 925 in FIG. 9. In some examples, the method 1000 includes writing at least one hardware register to programmably change a frequency of pulses between duty cycles. This is shown in waveform 920 of FIG. 9.

Figure 5A:
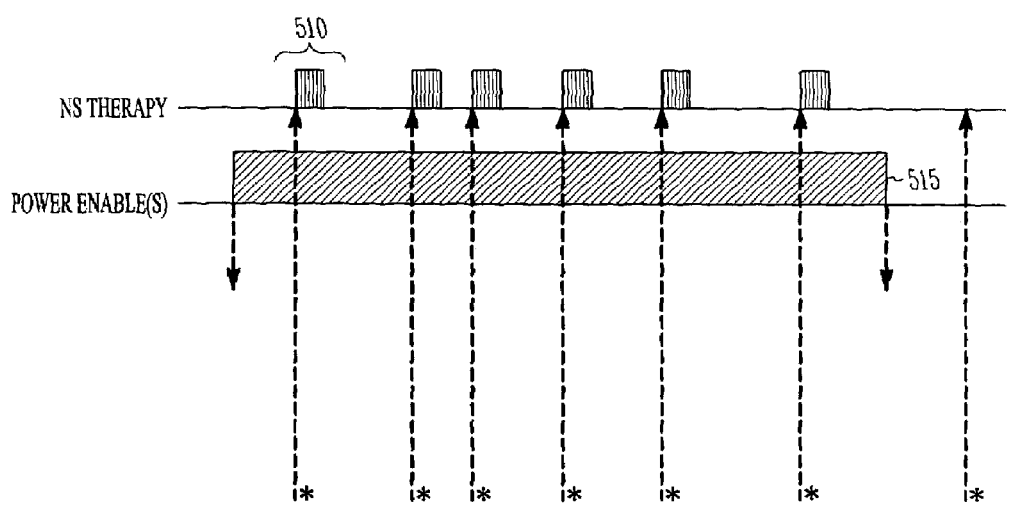
FIGS. 5A-C show further illustrations of pulses and the enable options.

Returning to FIG. 10, at 1015 the method includes applying power to a neural stimulation therapy source of the IMD during an active portion of a therapy duty cycle using the state machine, and removing power from the neural therapy source when exiting the active portion of a therapy duty cycle. In some examples, the active portion of the duty cycle is defined by a number of associated bursts of electrical stimulation pulses. This is illustrated in FIG. 5A. The active portion of the therapy duty cycle is defined by the six bursts of stimulation pulses. An inactive portion of the therapy duty cycle commences when delivery of the bursts has finished. Power is automatically applied to a neural therapy source when the bursts begin or a sufficient amount of time before the bursts begin to allow the neural therapy source to reach a powered-up state. Power is removed from the neural therapy source when the bursts end.

Figure 5B:
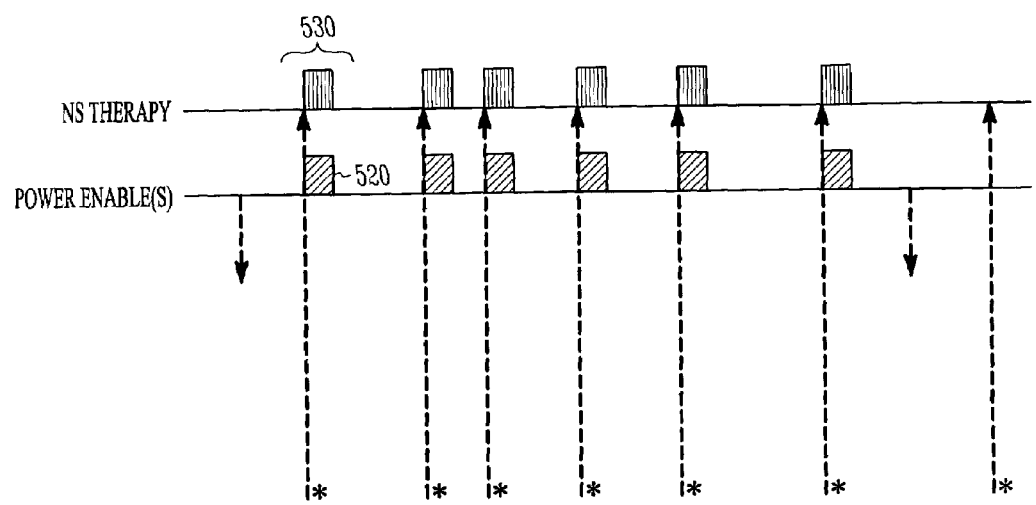

In some examples, the active portion of the duty cycle is defined by a burst of associated electrical neural stimulation pulses. This is illustrated in FIG. 5B. Power is applied during the active portion of the therapy duty cycle which begins when each burst begins, or a sufficient amount of time before each burst begins to allow the neural therapy source to reach a powered-up state. Power is removed during the inactive portion of the duty cycle which begins when each burst has finished.

Figure 5C:
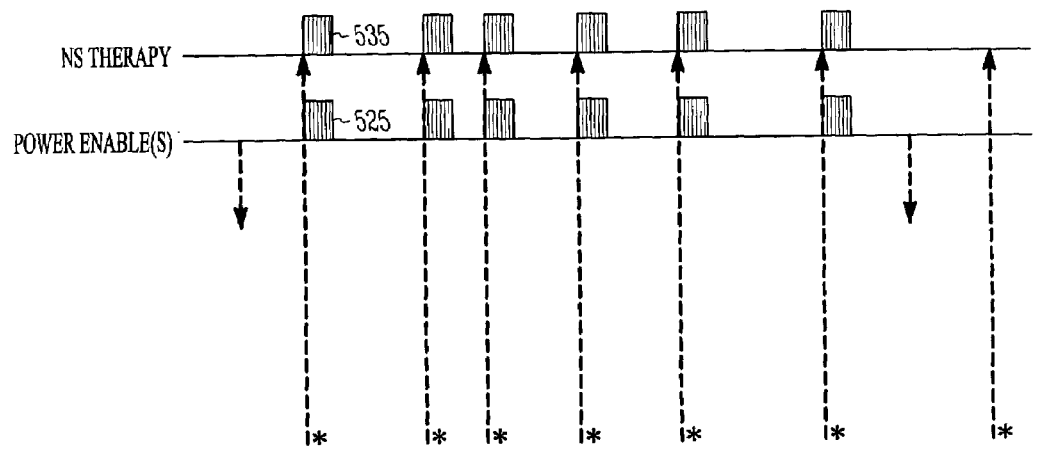

In some examples, the active portion of the duty cycle is during delivery of an electrical neural therapy stimulation pulse. The inactive portion is when a pulse is not being delivered. This is illustrated in FIG. 5C. Power is applied during an electrical neural therapy stimulation pulse and removed from the neural therapy source after the electrical neural therapy stimulation pulse.

In some examples, the method 1000 includes implementing NS therapy in an IMD that is capable of performing other functions as well. In some examples, the IMD is capable of one or more CFM functions. In some examples, the method 1000 further includes delivering an electrical pacing pulse to a pacing electrode in association with the electrical neural stimulation therapy.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations, or variations, or combinations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own.

What is claimed is:

1. An implantable medical device (IMD) comprising:
    a controller adapted to execute instructions included in firmware;
    a programmable neural therapy source adapted to provide programmable electrical neural stimulation therapy to at least one neural stimulation electrode; and
    a state machine separate from the controller and included in hardware circuitry coupled to the programmable neural therapy source, the state machine configured to implement a duty cycle of neural therapy including to automatically apply circuit power to the neural therapy source when neural therapy is initiated by a controller firmware instruction and automatically remove circuit power from the neural therapy source when neural therapy is terminated by a controller firmware instruction.

2. The IMD of claim 1, wherein, when neural therapy is initiated by a firmware instruction, the state machine is adapted to automatically apply power to the neural therapy source during an active portion of a therapy duty cycle and to remove power from the neural therapy source when exiting the active portion of a therapy duty cycle.

3. The IMD of claim 2, wherein the state machine is adapted to apply power to the neural therapy source during an electrical neural therapy stimulation pulse and to remove power from the neural therapy source after the electrical neural therapy stimulation pulse.

4. The IMD of claim 2, wherein the state machine is adapted to apply power to the neural therapy source during a burst of associated electrical neural therapy stimulation pulses, and to remove power from the neural therapy source after the burst of electrical neural therapy stimulation pulses.

5. The IMD of claim 2, wherein the programmable neural therapy source includes a programmable current source, and wherein the state machine is adapted to apply power to the programmable current source during an envelope of time that begins an amount of time before the active portion of a therapy duty cycle that is sufficient to activate the programmable current source, and to remove power when the active portion of a therapy duty cycle ends.

6. The IMD of claim 5, wherein the state machine is adapted to apply power to the programmable current source within a range of approximately ten microseconds (10 μs) to five milliseconds (5 ms) before the active portion of a therapy duty cycle.

7. The IMD of claim 1, wherein the state machine includes one or more hardware registers writeable by the controller, and wherein the hardware registers include one or more fields that define the programmable electrical neural stimulation therapy including a field to program one or more electrical stimulation pulses to be included in an active portion of a therapy duty cycle and one or more pulse times to be included in an inactive portion of a therapy duty cycle.

8. The IMD of claim 7, wherein at least one hardware register includes a field to program one or more duty cycles to issue upon a neural therapy trigger from the controller.

9. The IMD of claim 7, wherein at least one hardware register includes a field to programmably ramp a number of electrical stimulation pulses to be included in the active portion of a therapy duty cycle.

10. The IMD of claim 7, wherein at least one hardware register includes a field to program a frequency of electrical stimulation pulses to be included in a therapy duty cycle.

11. The IMD of claim 7, wherein at least one hardware register includes a field to programmably change a frequency of pulses between duty cycles.

12. The IMD of claim 7, wherein at least one hardware register includes a field to programmably change an amplitude of electrical stimulation pulses included in the active portion of a therapy duty cycle.

13. The IMD of claim 7, wherein at least one hardware register includes a field to program an amplitude envelope of electrical stimulation pulses included in a duty cycle.

14. The IMD of claim 7, wherein at least one hardware register includes a field to programmably ramp amplitudes of electrical stimulation pulses to be included in the active portion of a therapy duty cycle.

15. The IMD of claim 1 further including:
a cardiac signal sensing circuit operable to produce a signal representative of cardiac activity of a subject; and
a pacing circuit for delivering an electrical stimulation pulse to a pacing electrode.

16. A method comprising the acts of:
initiating neural stimulation therapy using at least one instruction included in firmware of an implantable medical device (IMD);
delivering, in response to the firmware instruction and using a state machine included in hardware in the IMD separate from a controller of the IMD, an electrical neural stimulation therapy to a non-cardiac neural stimulation electrode using a state machine included in hardware in the IMD; and
implementing, with the hardware state machine, a neural therapy duty cycle of neural therapy including applying circuit power to a neural stimulation therapy source of the IMD using the state machine and removing circuit power from the neural therapy source when neural therapy is terminated by the firmware.

17. The method of claim 16, wherein applying power further includes powering the neural therapy source during an active portion of a therapy duty cycle and removing power from the neural therapy source when exiting the active portion of a therapy duty cycle.

18. The method of claim 17, wherein powering includes powering the neural therapy source during an electrical neural therapy stimulation pulse and removing power from the neural therapy source after the electrical neural therapy stimulation pulse.

19. The method of claim 17, wherein powering includes powering the neural therapy source during a burst of associated electrical neural stimulation pulses and removing power from the neural therapy source after the burst of electrical neural therapy stimulation pulses.

20. The method of claim 17, wherein powering includes:
powering the neural stimulation therapy source during a time prior to the active portion to activate the neural stimulation therapy source that is sufficient to activate the programmable current source; and
removing power when the active portion of a therapy duty cycle ends.

21. The method of claim 16, wherein automatically delivering an electrical neural stimulation therapy includes writing at least one hardware register in the state machine to program an electrical neural stimulation therapy.

22. The method of claim 21 including writing at least one hardware register to program one or more electrical stimulation pulses to be included in the active portion of a therapy duty cycle and one or more pulse times to be included in an inactive portion of a therapy duty cycle.

23. The method of claim 21 including writing at least one hardware register to program one or more duty cycles to issue upon a neural therapy trigger from a firmware instruction.

24. The method of claim 21 including writing at least one hardware register to programmably ramp a number of electrical stimulation pulses to be included in the active portion of a therapy duty cycle.

25. The method of claim 21 including writing at least one hardware register to program an amplitude envelope function of electrical stimulation pulses in a duty cycle.

26. The method of claim 21 including writing at least one hardware register to programmably change a time between electrical stimulation pulses within a same burst.

27. The method of claim 16, further including delivering an electrical pacing pulse to a pacing electrode in association with the electrical neural stimulation therapy.

* * * * *